(12) United States Patent
Seal et al.

(10) Patent No.: US 9,714,405 B2
(45) Date of Patent: Jul. 25, 2017

(54) BIOPROCESSING CONTAINER TUBE SYSTEM AND METHOD OF USE

(71) Applicant: Pall Corporation, Port Washington, NY (US)

(72) Inventors: Michael B. Seal, Portsmouth (GB); Nicholas L. Yoward, Hampshire (GB)

(73) Assignee: PALL CORPORATION, Port Washington, NY (US)

( * ) Notice: Subject to any disclaimer, the term of this patent is extended or adjusted under 35 U.S.C. 154(b) by 259 days.

(21) Appl. No.: 14/685,916

(22) Filed: Apr. 14, 2015

(65) Prior Publication Data

US 2016/0304822 A1    Oct. 20, 2016

(51) Int. Cl.
| | |
|---|---|
| C12M 1/00 | (2006.01) |
| C12M 3/00 | (2006.01) |
| B01L 3/00 | (2006.01) |
| B01F 15/00 | (2006.01) |
| B01L 9/00 | (2006.01) |
| B01F 7/16 | (2006.01) |

(52) U.S. Cl.
CPC ............ *C12M 23/14* (2013.01); *B01F 7/162* (2013.01); *B01F 15/0085* (2013.01); *B01F 15/00772* (2013.01); *B01L 3/505* (2013.01); *B01L 9/00* (2013.01); *C12M 23/40* (2013.01); *C12M 23/48* (2013.01); *B01L 3/52* (2013.01); *B01L 2200/087* (2013.01); *B01L 2300/0609* (2013.01); *B01L 2300/0832* (2013.01); *B01L 2300/0851* (2013.01); *B01L 2300/0858* (2013.01); *B01L 2300/123* (2013.01)

(58) Field of Classification Search
CPC ...... C12M 23/02; C12M 23/14; C12M 23/40; C12M 23/48; C12M 23/50
See application file for complete search history.

(56) References Cited

U.S. PATENT DOCUMENTS

| | | | |
|---|---|---|---|
| 5,988,422 A | 11/1999 | Vallot | |
| 6,019,432 A | 2/2000 | Bonerb | |
| 7,284,579 B2 | 10/2007 | Elgan et al. | |
| 7,588,161 B2 | 9/2009 | Elgan et al. | |
| 7,992,598 B2 | 8/2011 | Elgan et al. | |
| 8,272,410 B2 | 9/2012 | Elgan et al. | |
| 8,381,789 B2 | 2/2013 | Payne | |
| 8,569,050 B1 * | 10/2013 | Ericsson | C12N 1/12 435/292.1 |
| 2004/0261889 A1 | 12/2004 | Elgan | |
| 2006/0237480 A1 | 10/2006 | Miller et al. | |
| 2009/0236344 A1 * | 9/2009 | McRobbie | B65D 75/26 220/495.06 |

(Continued)

FOREIGN PATENT DOCUMENTS

| | | |
|---|---|---|
| EP | 2 103 548 A1 | 9/2009 |
| EP | 2 123 745 B1 | 11/2009 |

(Continued)

OTHER PUBLICATIONS

European Patent Office, Extended European Search Report in counterpart European Patent Application No. 16156514.8, mailed Jul. 28, 2016.

*Primary Examiner* — Nathan Bowers
(74) *Attorney, Agent, or Firm* — Jeremy Jay

(57) ABSTRACT

Bioprocessing container tube management systems, totes including the systems, and methods of using the systems, are disclosed.

5 Claims, 6 Drawing Sheets

(56) References Cited

U.S. PATENT DOCUMENTS

2013/0244322 A1* 9/2013 Henon .................. C12M 23/14
                                                              435/325

FOREIGN PATENT DOCUMENTS

| EP | 2 607 474 A1 | 6/2013 |
| WO | WO 02/074141 A1 | 9/2002 |
| WO | WO 2013/171340 A2 | 11/2013 |

* cited by examiner

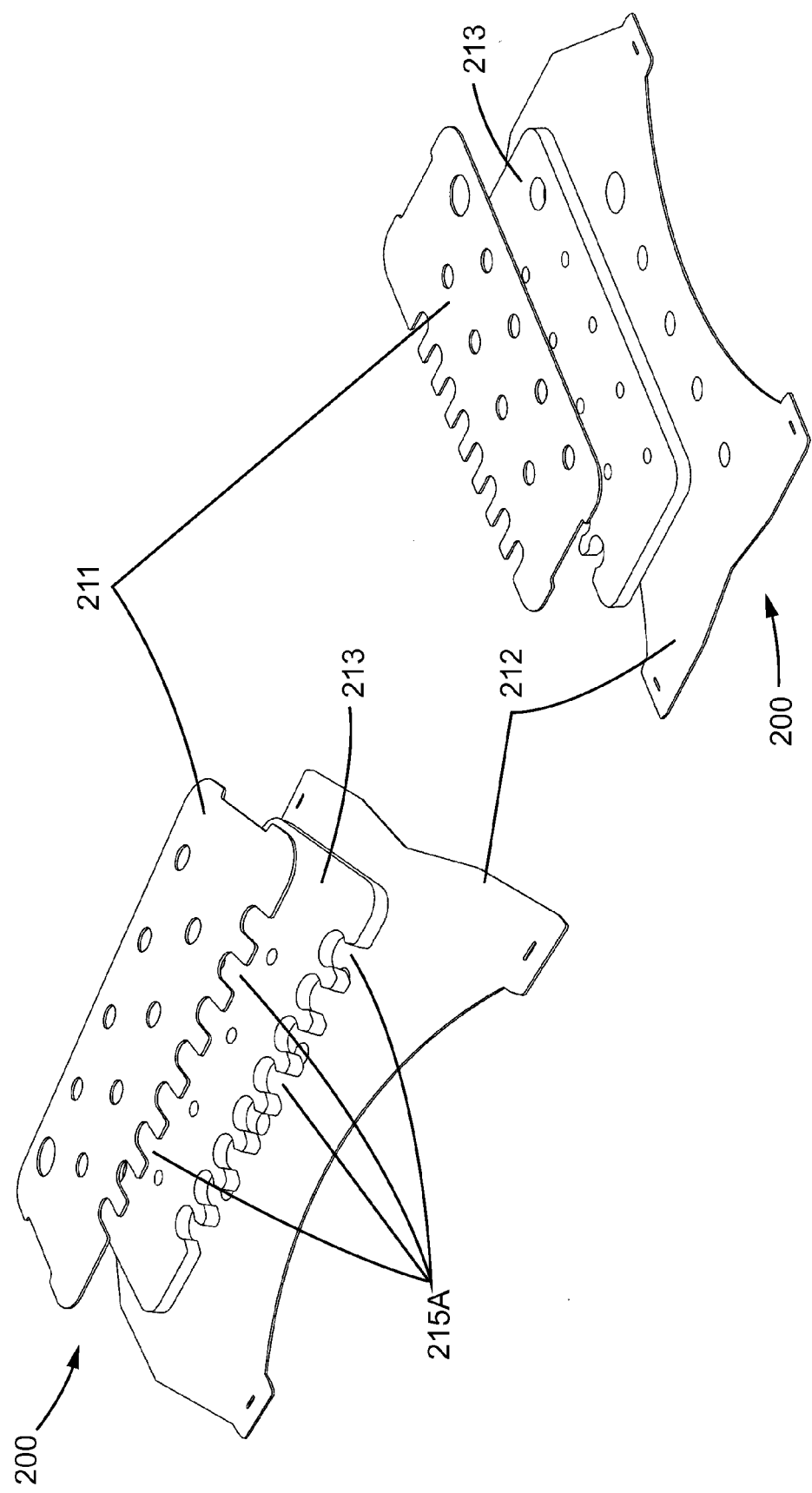

us 9,714,405 B2

BIOPROCESSING CONTAINER TUBE SYSTEM AND METHOD OF USE

BACKGROUND OF THE INVENTION

Bioreactor bags can be packaged with tubing and connectors. Some bioreactor bags are large (e.g., about 1000 L or more) and unwieldy to handle and/or set up in a tote.

The present invention provides for ameliorating at least some of the disadvantages of the prior art. These and other advantages of the present invention will be apparent from the description as set forth below.

BRIEF SUMMARY OF THE INVENTION

An embodiment of the invention provides a bioprocessing container tube management system comprising (a) a flexible inflatable bioprocessing bag comprising a top wall, a bottom wall, and opposing side walls, providing an interior volume therein; (b) a tube support comprising a plate including a plurality of slots, wherein the tube support is attached to a wall of the bag; and, (c) a plurality of hollow tubes attached to the bag and in fluid communication with the interior volume of the bag, wherein the tubes are retained in the slots of the tube support.

In another embodiment, a tote for a bioprocessing bag comprises (a) a compartment for receiving the bioprocessing container tube management system comprising a bioprocessing bag and a tube support, the compartment including at least one beam, preferably, a horizontally arranged beam; and (b) a tube management frame engageable with the tube support of the bioprocessing container tube management system, wherein the tube management frame is attached to the beam of the compartment for receiving the bioprocessing container tube management system, and, once the tube management frame is engaged with the tube support and the bioprocessing bag is inflated, the frame pivots, guiding the plurality of tubes to a desired position on the tote.

In yet another embodiment, a bioprocessing container tote system is provided comprising (a) the bioprocessing container tube management system comprising a bioprocessing bag and a tube support; (b) a tote for the bioprocessing bag, the tote further comprising a tube management frame engageable with the tube support, wherein the tube management frame is attached to the tote, and, once the tube management frame is engaged with the tube support and the bag is inflated, the tube management frame pivots, guiding the plurality of tubes to a desired position on the tote.

A method of setting up a bioprocessing container on a tote according to an embodiment of the invention comprises (a) loading the bioprocessing container tube management system comprising a bioprocessing bag and a tube support in the tote, the tote including a tube management frame engageable with the tube support, wherein the tube management frame is attached to the tote, and, once the tube management frame is engaged with the tube support, the tube management frame pivots when the bioprocessing bag is inflated, guiding the plurality of tubes to a desired position on the tote; and, (b) inflating the bioprocessing bag until the plurality of tubes are guided to a desired position on the tote.

BRIEF DESCRIPTION OF THE SEVERAL VIEWS OF THE DRAWING(S)

FIG. 1 is a diagrammatic view of an embodiment of a bioprocessing container tube management system including a bioprocessing bag and a tube support accommodating tubes according to an embodiment of the present invention, further illustrating a tube management frame engaged with the tube support, wherein the tube management system is inserted in an embodiment of a bioprocessing container tote system, the Figure also showing the operation of the bioprocessing container tube management system such that the frame pivots when the bag is expanded and the tubes have been guided to the desired position on the tote.

FIG. 6 shows an exploded view of one arrangement for a tube support comprising 2 panels and an intermediate layer.

DETAILED DESCRIPTION OF THE INVENTION

Figure 1:
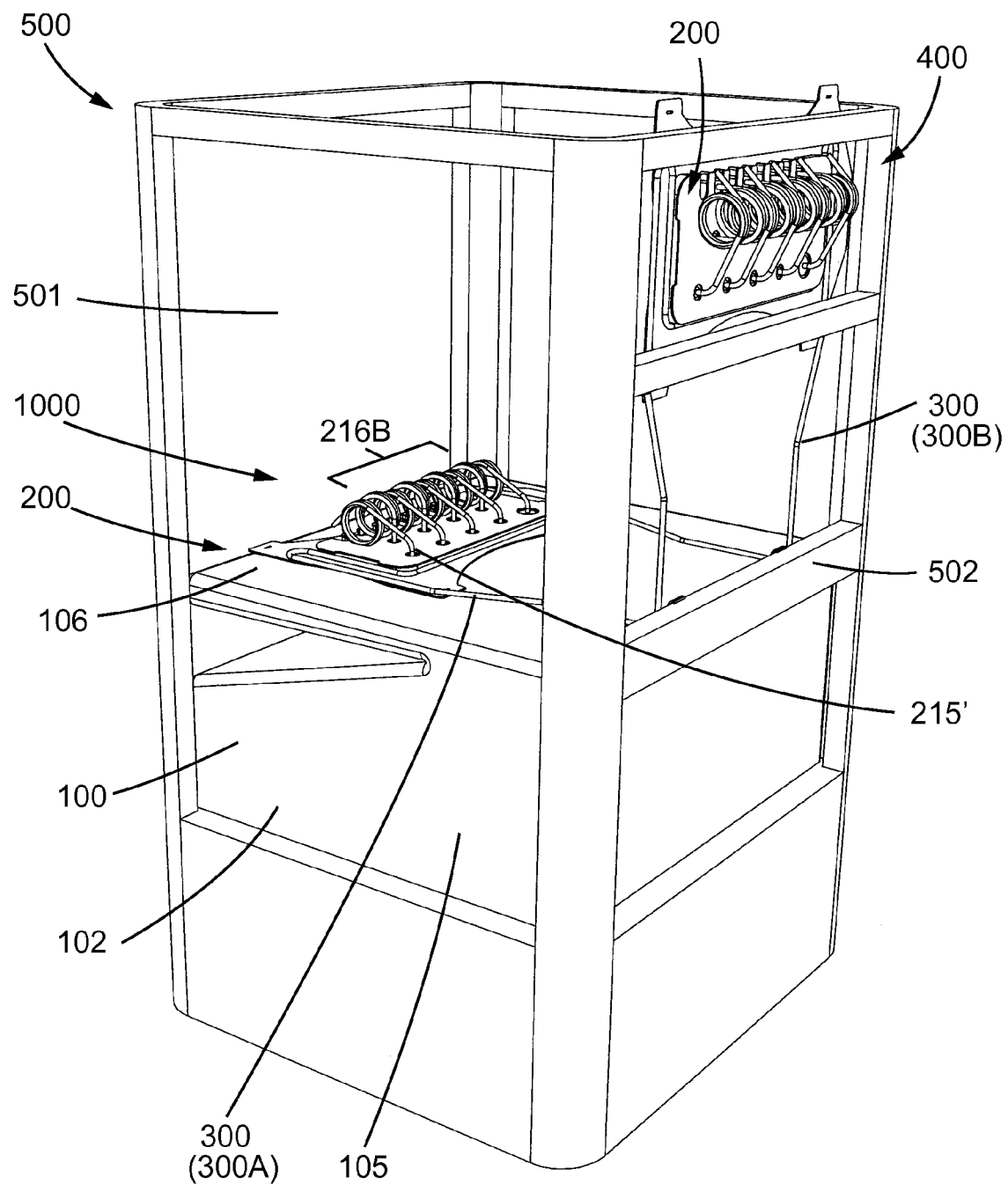

In accordance with an embodiment of the present invention, a bioprocessing container tube management system is provided comprising (a) a flexible inflatable bioprocessing bag comprising a top wall, a bottom wall, and opposing side walls, providing an interior volume therein; (b) a tube support comprising a plate including a plurality of slots, wherein the tube support is attached to a wall of the bag; and, (c) a plurality of hollow tubes attached to the bag and in fluid communication with the interior volume of the bag, wherein the tubes are retained in the slots of the tube support. In a preferred embodiment, the tube supported is attached to a side wall of the bag.

In an embodiment of the system, the tube support comprises first and second panels and a foam layer between the panels.

In another embodiment, a tote for a bioprocessing container comprises (a) a compartment for receiving the bioprocessing container tube management system comprising a bioprocessing bag and a tube support, the compartment including at least one beam, preferably, a horizontally arranged beam; and (b) a tube management frame engageable with the tube support of the bioprocessing container tube management system, wherein the tube management frame is attached to the beam of the compartment for receiving the bioprocessing container tube management system, and, once the tube management frame is engaged with the tube support and the bioprocessing bag is inflated, the frame pivots, guiding the plurality of tubes to a desired position on the tote.

In yet another embodiment, a bioprocessing container tote system is provided comprising (a) the bioprocessing container tube management system comprising a bioprocessing bag and a tube support; (b) a tote for the bioprocessing bag, the tote further comprising a tube management frame engageable with the tube support, wherein the tube management frame is attached to the tote, and, once the tube management frame is engaged with the tube support and the bag is inflated, the tube management frame pivots, guiding the plurality of tubes to a desired position on the tote.

A method of setting up a bioprocessing bag on a tote according to an embodiment of the invention comprises (a) loading the bioprocessing container tube management system comprising a bioprocessing bag and a tube support in the tote, the tote including a tube management frame engageable with the tube support, wherein the tube management frame is attached to the tote, and, once the tube management frame is engaged with the tube support, the tube management frame pivots when the bioprocessing bag is inflated, guiding the plurality of tubes to a desired position on the tote; and, (b) inflating the bioprocessing bag until the plurality of tubes are guided to a desired position on the tote.

Advantageously, bioprocessing containers can be filled easily, with little or no creases, and the tubes can be orderly arranged and located at a desired location on the tote, for ease of use. Embodiments of the invention are suitable for use with bioprocessing containers having any volume, and are especially suitable for bags with larger volumes, e.g., having a volume of at least about 500 L, or at least about 1000 L, or greater.

Each of the components of the invention will now be described in more detail below, wherein like components have like reference numbers.

FIG. 1 shows, diagrammatically, an embodiment of a bioprocessing container tube management system 1000 comprising a flexible inflatable bioprocessing bag 100 (shown deflated), having walls defining an interior volume, a tube support 200 comprising a plate including a plurality of slots, wherein the tube support is attached to a wall (shown attached to sidewall 106) of the bag; and a plurality of hollow tubes 216B attached to the bag and in fluid communication with the interior volume of the bag, wherein the tubes are retained in the slots of the tube support, and one end 215' of the tubes is attached to the bag. FIG. 1 also shows a tube management frame 300 engaged with the tube support, wherein the tube management system is inserted in a bag receiving compartment 501 of the bioprocessing container tote 500, and the frame 300 is attached to a beam 502 of the bag receiving compartment of the tote and engaged with the tube support, the Figure also showing the operation of the bioprocessing container tube management system such that the frame 300 pivots from position 300A to position 300B when the bag is expanded and the tubes have been guided to the desired position 400 on the tote.

Figure 2:
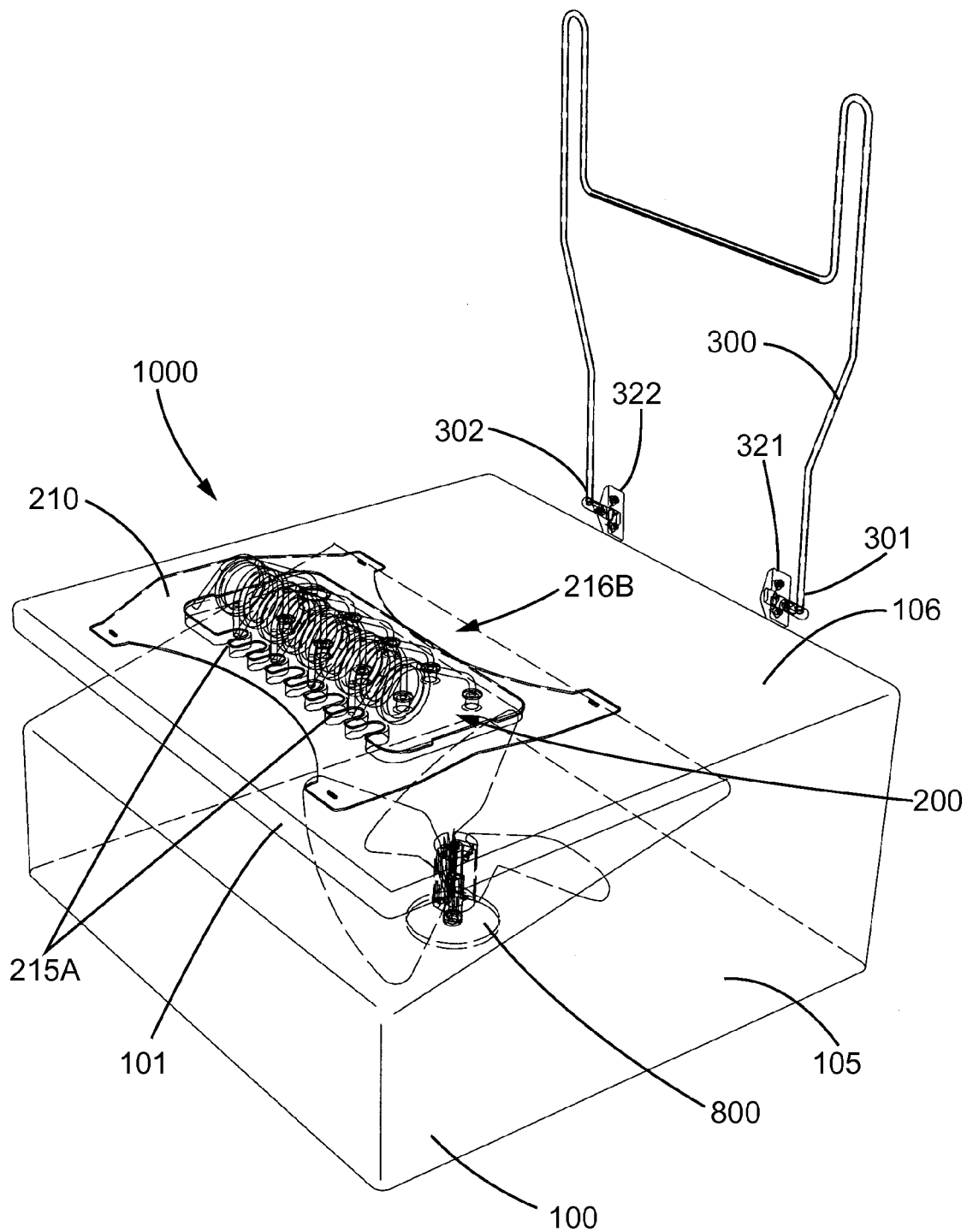
FIG. 2 is a perspective diagrammatic view of the embodiment of the bioprocessing container tube management system including the bioprocessing bag and the tube support accommodating tubes as shown in FIG. 1, further showing the tube management frame for attachment to the tote, wherein the bioprocess bag is not inflated, and the tube management frame is not engaged with the tube support.

FIG. 2 shows, diagrammatically, in more detail than in FIG. 1, an embodiment of a bioprocessing container tube management system 1000 comprising (a) a flexible inflatable bioprocessing bag 100 comprising a top wall 101, a bottom wall 102, and opposing side walls 103, 104, 105, 106, providing an interior volume therein; (b) a tube support 200 comprising a plate 210 including a plurality of slots 215A, wherein the tube support is attached to a wall (shown attached to sidewall 106) of the bag; and, (c) a plurality of hollow tubes 216B attached to the bag and in fluid communication with the interior volume of the bag, wherein the tubes are retained in the slots of the tube support.

As will be described detail below, FIG. 2 (and, particularly, FIGS. 3-5) also show a tube management frame 300 engageable with the tube support 200, the frame 300 also including pivots 311 and 312 mounted to ends 301, 302 of the frame, the pivots inserted into respective pivot mounting blocks 321 and 322, wherein the tube management frame is attachable to a tote 500, and, once the frame is engaged with the tube support and the bag is inflated, the frame pivots, guiding the support and plurality of retained tubes to a desired position on the tote.

Figure 3:
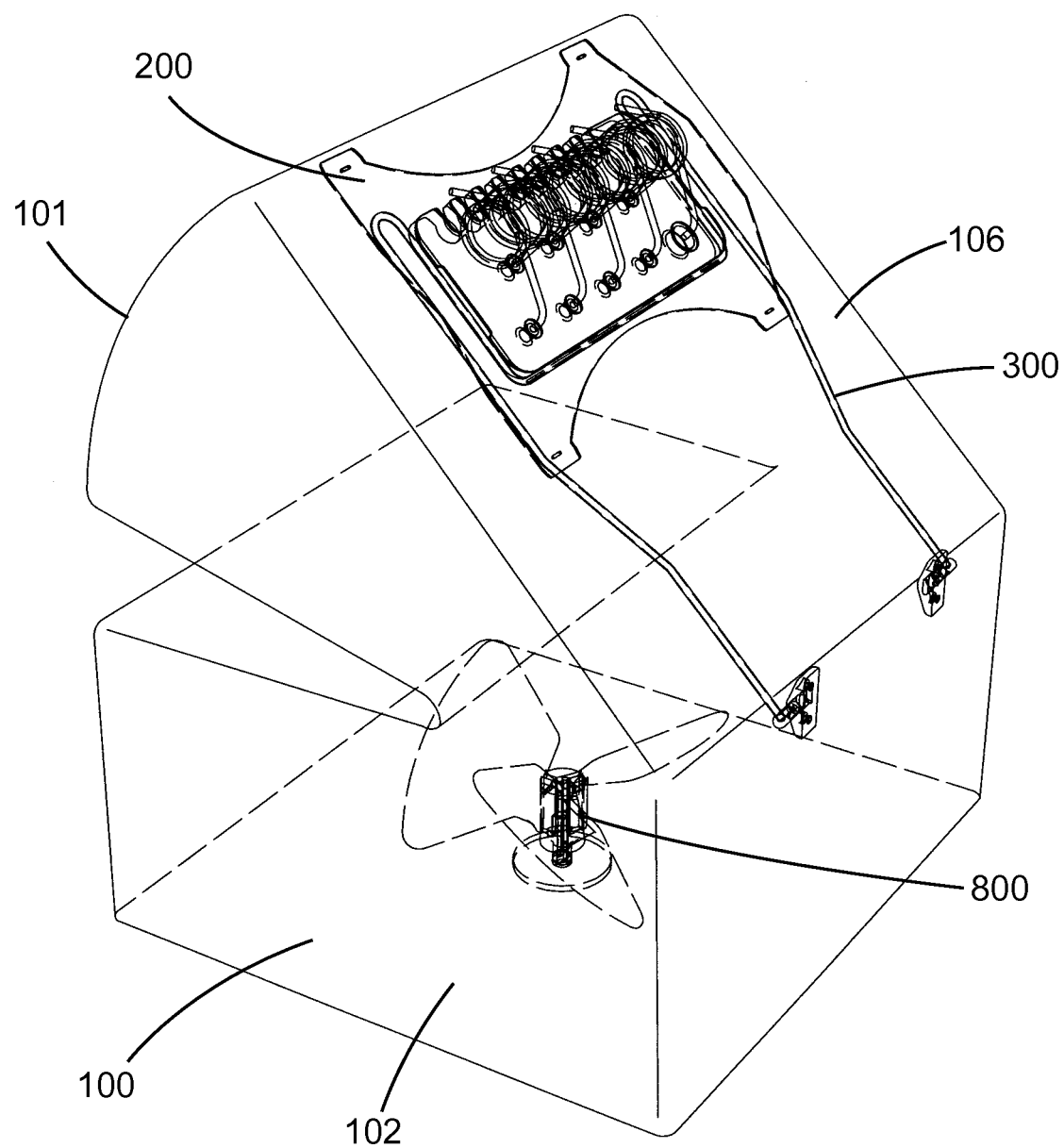
FIG. 3 shows a perspective diagrammatic view of the bioprocessing container system and tube management frame shown in FIG. 2, wherein the tube management frame is engaged with the tube support, and the bag is partially inflated, such that the frame pivots.
Figure 4:
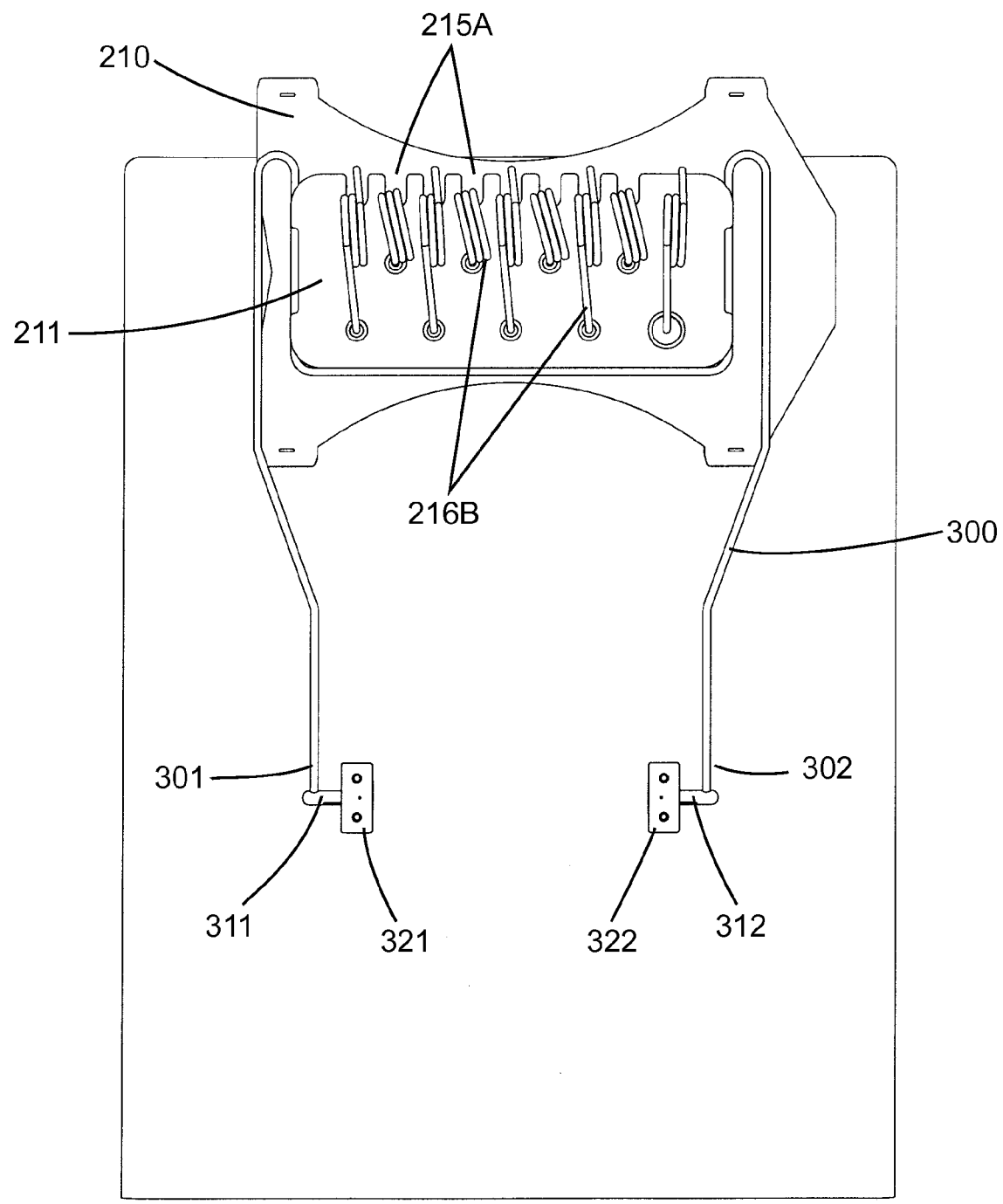
FIG. 4 shows a rear view of the bioprocessing container system and tube management frame shown in FIG. 3, also showing portions of the tube management frame inserted in a groove on the short edges and lower long side of the tube support, also showing including pivots mounted to ends of the frame, the pivots inserted into respective pivot mounting blocks for attachment to the tote.

In accordance with the embodiment illustrated in FIG. 3, the tube management frame 300 is engaged with the tube support 200, and the bag 100 is partially inflated, the frame pivots, guiding the tube support and plurality of tubes toward a desired position on the tote.

Figure 5:
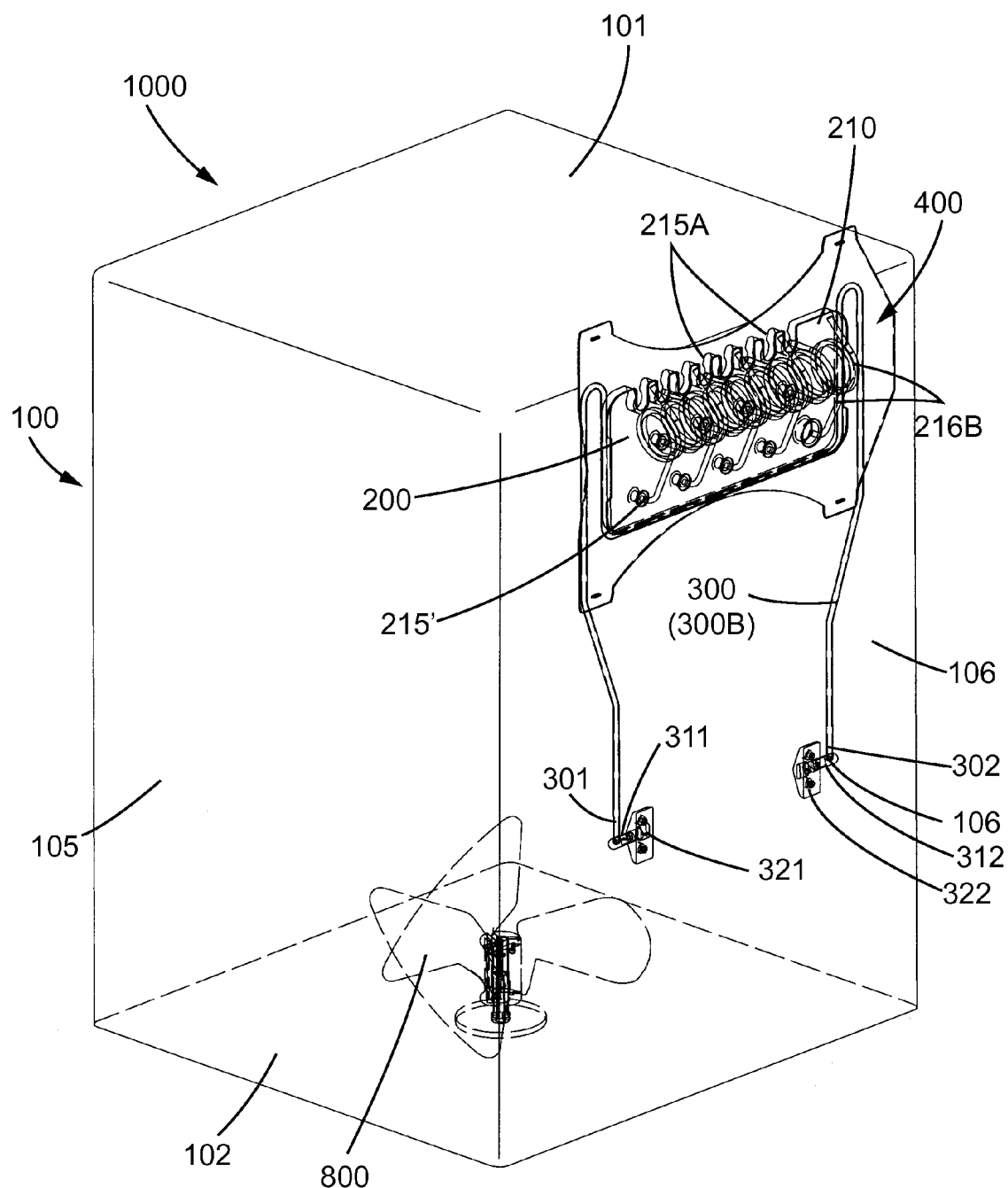
FIG. 5 shows a perspective diagrammatic view of an embodiment of the bioprocessing container system and tube management frame, wherein the tube management frame is engaged with the tube support, and the bag is fully inflated, such that the tubes have been guided to the desired position.

FIGS. 1 and 5 show the fully inflated bag 50 of the tube management system 1000 wherein the tubes 216B have been guided to the desired position 400 on the tote 500.

FIG. 6 shows an exploded view of an illustrative arrangement of the tube support 200, wherein plate 210 comprises upper panel 211 and lower panel 212, and an intermediate layer 213 between the panels. In this illustrative arrangement, the intermediate layer 213 is shorter in width and length than that of the panels 211 and 212, providing a groove on the short edge and lower end of the long side of the support for insertion of portions of the tube management frame (as shown in, for example, FIG. 4).

A variety of materials are suitable for use in the tube management frame 300 (e.g., plastic or metal), and the frame can be hollow, tubular, or solid, and have any cross-sectional form (e.g., circular, oval, square, or hexagonal).

While the illustrated embodiments show two pivots 311, 312, each mounted to an end of the tube management frame, the tube management frame can be set up with a single, or more than two, pivots. If a single pivot is used, it can be positioned centrally, or offset from the center line.

In the illustrated embodiments, each pivot 311,312 is inserted into a separate pivot mounting block 321,322, and pivot mounting blocks can be made from a variety of materials (e.g., plastic or metal). Preferably, each pivot mounting block includes a rotary damper allowing the frame to drop slowly from a vertical position, e.g., to improve safety during use.

The tube management frame 300 can be attached to the tote 500 at a variety of locations, using a single, or two or more, pivot mounting blocks as noted above. Typically, the tube management frame is attached to a beam in the tote, illustrated as a horizontally arrangement beam 502 in compartment 501 in the embodiment of the tote 500 shown in FIG. 1.

The bioprocessing container 100 (or biocontainer or bioprocessing bag), which is flexible (e.g., plastic), can have any suitable form (e.g., cylindrical (having, for example, a single continuous side wall), square, or rectangular), and in the Figures is illustrated as having a generally rectangular cuboid form with a plurality of side walls.

Typically, and as shown in FIGS. 2, 3, and 5, the bioprocessing container includes an impeller 800. Suitable impellers are known in the art.

The bioprocessing bag can have any suitable number and locations of tubes (conduits), ports, and flow control devices (e.g., valves and/or clamps) (ports and flow control devices not shown). Additional ports, can include, for example, one or more of any of the following ports: a liquid inlet port, a gas inlet port, a gas outlet port, a powder inlet port, an acid/base inlet port, a probe port, and/or a sample port. Suitable bag materials, tubes, ports, and flow control devices are known in the art.

A variety of fluids can be processed and/or prepared (including mixing) in accordance with embodiments of the invention. Applications include, for example, cell culture (e.g., including batch and fed-batch operations of suspension and adherent cell lines), preparing sterile fluids for the pharmaceutical and/or biopharmaceutical industries, including drugs, vaccines, and intravenous fluids, antibody- and/or protein-containing fluids, and/or fluids for the food and beverage industry. Fluids mixed according to embodiments of the invention can also used, for example, as media and/or buffers such as chromatography buffers.

For example, a method for preparing a mixed fluid used in bioprocessing comprises (a) passing at least one fluid and at least one component to be mixed with the fluid through one or more ports into an embodiment of the inflated biocontainer, and (b) rotating the impeller, and mixing the at least one fluid and the at least one component to be mixed with the fluid, and producing the mixed fluid, which can be used as desired.

The following example further illustrates the invention but, of course, should not be construed as in any way limiting its scope.

EXAMPLE

This example demonstrates the operation of an embodiment of the bioprocessing container tube management system in a tote, wherein a 1000 L bioprocessing bag is filled easily, with little or no creases, and the tubes can be orderly arranged and located at a desired location on the tote. An embodiment of the bioprocessing container tube management system, including a flexible inflatable bioprocessing bag and an impeller is placed in a tote, such that the lower portion of the impeller housing passes through an opening in the floor of the tote.

The tube management frame is made from tubular stainless steel and pivotably mounted on a horizontally arranged beam on the tote. The tube management support has upper and lower polymeric (high density polyethylene (HDPE)) panels with a polyethylene foam layer between, and connected to, the polymeric panels. The foam layer is shorter in width and length than the width and length of the panels, providing a "recessed groove" on the short edges and lower long side of the support for insertion of portions of the tube management frame.

The tube management frame, which is attached to the tote, is pivoted downwardly and the frame is engaged with the tube support by insertion of portions of the frame into the recessed groove of the tube support.

The bag is inflated as air passes through a sterilizing vent filter and through a port at the bottom of the bag. The bag is inflated and the frame pivots about 90° such that the tubes arrive at the desired location at the corresponding "cut out" in the tote.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A bioprocessing container tote system comprising:
    (a) a bioprocessing container tube management system comprising:
        a flexible inflatable bioprocessing bag comprising a top wall, a bottom wall, and a opposing side walls, providing an interior volume therein;
        a tube support comprising a plate including a plurality of slots, wherein the tube support is attached to a wall of the bag; and,
        a plurality of hollow tubes attached to the bag and in fluid communication with the interior volume of the bag, wherein the tubes are retained in the slots of the tube support;
    (b) a tote for the bioprocessing bag, the tote further comprising a tube management frame engageable with the tube support, wherein the tube management frame is attached to the tote, and, once the tube management frame is engaged with the tube support and the bioprocessing bag is inflated, inflation causes the tube management frame to pivot, guiding the plurality of tubes to a desired position on the tote.

2. The bioprocessing container tote system of claim 1, wherein the tube support comprises first and second panels and a foam layer between the panels.

3. The bioprocessing container tote system of claim 1, wherein the bioprocessing bag has a volume of at least about 500 L.

4. The bioprocessing container tote system of claim 1, the tote further comprising:
   (a) a compartment for receiving the bioprocessing container tube management system comprising the bioprocessing bag and the tube support, the compartment including at least one beam.

5. A method of setting up a bioprocessing bag on a tote comprising:
   (a) loading a bioprocessing container tube management system comprising:
      a flexible inflatable bioprocessing bag comprising a top wall, a bottom wall, and a opposing side walls, providing an interior volume therein;
      a tube support comprising a plate including a plurality of slots, wherein the tube support is attached to a wall of the bag; and,
      a plurality of hollow tubes attached to the bag and in fluid communication with the interior volume of the bag, wherein the tubes are retained in the slots of the tube support into the tote, the tote including a tube management frame engageable with the tube support, wherein the tube management frame is attached to the tote, and, once the tube management frame is engaged with the tube support, the tube management frame pivots when the bag is inflated, guiding the plurality of tubes to a desired position on the tote; and,
   (b) inflating the bioprocessing bag until the plurality of tubes are guided to a desired position on the tote.

* * * * *